(12) United States Patent
Siegert et al.

(10) Patent No.: US 8,350,063 B2
(45) Date of Patent: Jan. 8, 2013

(54) METHOD FOR SEPARATING TIOXANE FROM A TRIOXANE/FORMALDEHYDE/WATER MIXTURE BY MEANS OF PRESSURE CHANGE RECTIFICATION

(75) Inventors: Markus Siegert, Heidelberg (DE); Neven Lang, Mannheim (DE); Laszlo Szarvas, Ludwigshafen (DE); Christoph Sigwart, Weinheim (DE); Franz Niklaus Windlin, Heidelberg (DE); Eckhard Stroefer, Mannheim (DE)

(73) Assignee: BASF SE, Ludwigshafen (DE)

( * ) Notice: Subject to any disclaimer, the term of this patent is extended or adjusted under 35 U.S.C. 154(b) by 470 days.

(21) Appl. No.: 12/682,294

(22) PCT Filed: Sep. 22, 2008

(86) PCT No.: PCT/EP2008/062620
§ 371 (c)(1),
(2), (4) Date: Apr. 9, 2010

(87) PCT Pub. No.: WO2009/047109
PCT Pub. Date: Apr. 16, 2009

(65) Prior Publication Data
US 2010/0270140 A1   Oct. 28, 2010

(30) Foreign Application Priority Data
Oct. 9, 2007   (EP) .................................... 07118103

(51) Int. Cl.
C07D 323/06   (2006.01)
C07D 45/00   (2006.01)
B01D 3/10   (2006.01)

(52) U.S. Cl. ............ 549/368; 568/449; 203/74; 203/75; 203/77; 203/80

(58) Field of Classification Search .................. 549/368; 568/449; 203/74, 75, 77, 78, 80
See application file for complete search history.

(56) References Cited

U.S. PATENT DOCUMENTS
6,200,429 B1   3/2001   Freyhof et al.
6,610,888 B1   8/2003   Strofer et al.
2007/0272540 A1   11/2007   Siegert et al.

FOREIGN PATENT DOCUMENTS
| CA | 2673572 A1 | 7/2008 |
| DE | 1668867 A1 | 12/1971 |
| DE | 19732291 A1 | 1/1999 |
| DE | 19925870 A1 | 12/2000 |
| WO | WO-2005/063733 A1 | 7/2005 |
| WO | WO-2008/090169 A1 | 7/2008 |

OTHER PUBLICATIONS

U.S. Appl. No. 12/523,741.
U.S. Appl. No. 12/304,223.

Primary Examiner — Andrew D. Kosar
Assistant Examiner — Raymond Covington
(74) Attorney, Agent, or Firm — Connolly Bove Lodge & Hutz LLP

(57) ABSTRACT

A process for separating trioxane from a feed stream I comprising formaldehyde, trioxane and water, in which
a) a feed stream I comprising formaldehyde as main component and trioxane and water as secondary components is provided,
b) the feed stream I, a recycle stream V and a recycle stream VII comprising formaldehyde as main component and water and trioxane as secondary components are fed into a first distillation stage and distilled at a pressure of from 0.1 to 2.5 bar to give a stream II comprising formaldehyde as main component and water as secondary component and a stream III comprising trioxane as main component and water and formaldehyde as secondary components and a stream X comprising water, trioxane and formaldehyde,
c) the stream III is, if appropriate after removal of low boilers from the stream III in a low boiler removal stage, distilled in a second distillation stage at a pressure of from 0.2 to 17.5 bar, with the pressure in the second distillation stage being from 0.1 to 15 bar higher than the pressure in the first distillation stage, to give a stream IV consisting essentially of trioxane and the recycle stream V comprising trioxane as main component and water and formaldehyde as secondary components,
c1) the stream IV is purified in at least one further trioxane distillation stage at a pressure at the top of from 0.5 to 2 bar to give purified trioxane as side offtake stream XII in the enrichment section of the column,
d) the stream X and, if appropriate, a stream IX comprising water as main component are fed into a third distillation stage and distilled at a pressure of from 1 to 10 bar to give a stream VI consisting essentially of water and a recycle stream VII comprising formaldehyde as main component and water and trioxane as secondary components,
is described.

10 Claims, 2 Drawing Sheets

METHOD FOR SEPARATING TIOXANE FROM A TRIOXANE/FORMALDEHYDE/WATER MIXTURE BY MEANS OF PRESSURE CHANGE RECTIFICATION

RELATED APPLICATIONS

This application is a national stage application (under 35 U.S.C. §371) of PCT/EP2008/062620, filed Sep. 22, 2008, which claims benefit of European application 07118103.6, filed Oct. 9, 2007.

The invention relates to a process for separating trioxane from a trioxane/formaldehyde/water mixture and also a process for preparing trioxane which gives an improved process yield and improved product purity.

Trioxane is generally prepared by distillation of aqueous formaldehyde solution in the presence of acid catalysts. The trioxane is subsequently separated off from the distillate comprising formaldehyde and water by extraction with halogenated hydrocarbons such as methylene chloride or 1,2-dichoroethane or other solvents which are not miscible with water.

DE-A 1 668 867 describes a process for separating trioxane from mixtures comprising water, formaldehyde and trioxane by extraction with an organic solvent. Here, an extraction section comprising two subsections is supplied at one end with a customary organic, virtually water-immiscible extractant for trioxane and with water at the other end. The distillate from the trioxane synthesis which is to be separated is fed in between the two subsections. An aqueous formaldehyde solution is then obtained at the end at which the solvent is fed in and a virtually formaldehyde-free solution of trioxane in the solvent is obtained at the end at which the water is fed in. In one example, the distillate formed in the trioxane synthesis comprising 40% by weight of water, 35% by weight of trioxane and 25% by weight of formaldehyde is fed into the middle section of a pulse column, methylene chloride is fed in at the upper end of the column and water is fed in at the lower end of the column. Here, an about 25% strength by weight solution of trioxane in methylene chloride is obtained at the lower end of the column and an about 30% strength by weight aqueous formaldehyde solution is obtained at the upper end of the column.

A disadvantage of this mode of operation is that an extractant which has to be purified is obtained. Some of the extractants used are hazardous materials (classified as T or T+ according to the German hazardous materials regulations) whose handling requires particular precautions.

DE-A 197 32 291 describes a process for separating trioxane from an aqueous mixture consisting essentially of trioxane, water and formaldehyde, in which trioxane is separated off from the mixture by pervaporation and the trioxane-enriched permeate is separated by rectification into trioxane and an azeotropic mixture of trioxane, water and formaldehyde. In the example, an aqueous mixture comprising 40% by weight of trioxane, 40% by weight of water and 20% by weight of formaldehyde is separated in a first distillation column under atmospheric pressure into a water/formaldehyde mixture and an azeotropic trioxane/water/formaldehyde mixture. The azeotropic mixture is fed into a pervaporation unit which comprises a membrane composed of polydimethyl-siloxane with a hydrophobic zeolite. The trioxane-enriched mixture is separated in a second distillation column under atmospheric pressure into trioxane and once again an azeotropic mixture of trioxane, water and formaldehyde. This azeotropic mixture is recirculated to upstream of the pervaporation stage.

A disadvantage of this mode of operation is the very high capital costs for the pervaporation unit.

DE-A-07 101 198, which has an earlier priority date and is not a prior publication, describes a process for separating trioxane from a feed stream I comprising formaldehyde, trioxane and water, in which a) a feed stream I comprising formaldehyde as main component and trioxane and water as secondary components is provided, b) the feed stream I, a recycle stream V and a recycle stream VII comprising formaldehyde as main component and water and trioxane as secondary components are fed into a first distillation stage and distilled at a pressure of from 0.1 to 2.5 bar to give a stream II comprising formaldehyde as main component and water as secondary component and a stream III comprising trioxane as main component and water and formaldehyde as secondary components and a stream X comprising water, trioxane and formaldehyde, c) the stream III is, if appropriate after removal of low boilers from the stream III in a low boiler removal stage, distilled in a second distillation stage at a pressure of from 0.2 to 17.5 bar, with the pressure in the second distillation stage being from 0.1 to 15 bar higher than the pressure in the first distillation stage, to give a stream IV consisting essentially of trioxane and the recycle stream V comprising trioxane as main component and water and formaldehyde as secondary components, d) the stream X and, if appropriate, a stream IX comprising water as main component are fed into a third distillation stage and distilled at a pressure of from 1 to 10 bar to give a stream VI consisting essentially of water and a recycle stream VII comprising formaldehyde and water and trioxane.

It is an object of the invention to provide a process for separating trioxane from azeotropic trioxane/formaldehyde/water mixtures, which makes do without the extraction steps or pervaporation steps of the prior art, provides trioxane in high purity and preferably allows an improved process yield.

The object is achieved according to the invention by a process for separating trioxane from a feed stream I comprising formaldehyde, trioxane and water, in which a) a feed stream I comprising formaldehyde as main component and trioxane and water as secondary components is provided, b) the feed stream I, a recycle stream V and a recycle stream VII comprising formaldehyde as main component and water and trioxane as secondary components are fed into a first distillation stage and distilled at a pressure of from 0.1 to 2.5 bar to give a stream II comprising formaldehyde as main component and water as secondary component and a stream III comprising trioxane as main component and water and formaldehyde as secondary components and a stream X comprising water, trioxane and formaldehyde, c) the stream III is, if appropriate after removal of low boilers from the stream III in a low boiler removal stage, distilled in a second distillation stage at a pressure of from 0.2 to 17.5 bar, with the pressure in the second distillation stage being from 0.1 to 15 bar higher than the pressure in the first distillation stage, to give a stream IV consisting essentially of trioxane and the recycle stream V comprising trioxane as main component and water and formaldehyde as secondary components, c1) the stream IV is purified in at least one further trioxane distillation stage at a pressure at the top of from 0.5 to 2 bar to give purified trioxane as side offtake stream XII in the enrichment section of the column, d) the stream X and, if appropriate, a stream IX comprising water as main component are fed into a third distillation stage and distilled at a pressure of from 1 to 10 bar to give a stream VI consisting essentially of water and a recycle stream VII comprising formaldehyde as main component and water and trioxane as secondary components.

It has been found according to the invention that it is particularly advantageous to purify the stream IV again in at least one further trioxane distillation stage at a pressure at the top of from 0.5 to 2 bar. Here, purified trioxane is obtained as side offtake stream in the enrichment section of the column. This distillation is once again particularly preferably carried out in two stages, with the side offtake stream from the first column being fed to the bottom of the second column and high-purity trioxane being taken off from a side offtake of the second column.

The process yield can also be improved by binding formic acid comprised in the product mixture by addition of tertiary amines and/or imines and discharging the formic acid-amine salt formed in a liquid phase (ionic liquid) in distillation bottoms. This mode of operation is described in more detail below.

The main component is the component having the greater or greatest proportion by mass in the mixture in question. The proportion by mass of the main component in the respective mixture is preferably at least 40% by weight. A stream "consists essentially of" one or more components when it comprises at least 90% by weight of this or these component(s).

It is known that trioxane, formaldehyde and water form a ternary azeotrope which at a pressure of 1 bar has the composition 69.5% by weight of trioxane, 5.4% by weight of formaldehyde and 25.1% by weight of water.

According to the invention, this azeotrope is avoided by means of a pressure swing distillation in which a first distillation and a second distillation are carried out at different pressures. In a first distillation column which is operated at a relatively low pressure, the starting mixture is separated into a trioxane/water mixture having a low formaldehyde content III and an essentially trioxane-free formaldehyde/water mixture II. The formaldehyde/water mixture II can be recirculated to the trioxane synthesis. In a second distillation column operated at a higher pressure, the trioxane/formaldehyde/water mixture III obtained is separated into pure trioxane and a trioxane/formaldehyde/water mixture V having a lower trioxane content. The mixture V is recirculated to the first distillation column. According to the invention, a highly water-comprising mixture is also obtained in the first distillation column as side offtake stream X from which, in a third distillation column, essentially pure water VI is separated off and a trioxane/formaldehyde/water mixture VII having a lower water content is obtained. This mixture VII is recirculated to the first distillation column. A water-comprising stream IX obtained in the concentration of aqueous formaldehyde solution is preferably likewise fed to the third distillation column.

Suitable distillation columns are any distillation columns such as packed columns and tray columns. These can comprise any internals, packings or beds of random packing elements.

The pressure in the second distillation stage is from 0.1 to 15 bar higher than the pressure in the first distillation stage. This pressure difference is preferably from 1.0 to 10 bar, particularly preferably from 1.5 to 5 bar.

All pressures quoted are pressures at the top of the respective column.

The first distillation stage is carried out at a pressure of from 0.1 to 2.5 bar, preferably from 0.25 to 1.5 bar. The first distillation stage is generally carried out in a distillation column having at least 2, preferably from 2 to 50, particularly preferably from 4 to 25, theoretical plates. In general, the stripping section of this column comprises at least 25%, preferably from 50 to 90%, of the theoretical plates in this column.

The feed stream I generally comprises from 40 to 80% by weight of formaldehyde, from 20 to 59% by weight of water and from 1.0 to 30% by weight of trioxane. The feed stream I is preferably fed in gaseous form into the bottom of the first distillation column.

The stream II, which is generally obtained as bottom offtake stream from the first distillation column, generally comprises less than 5% by weight, preferably less than 2% by weight, of trioxane, particularly preferably less than 1% by weight of trioxane. For example, the stream II has the following composition: from 55 to 85% by weight of formaldehyde, from 15 to 45% by weight of water and from 0 to 5% by weight of trioxane. The stream III, which is generally obtained as overhead stream from the first distillation column, generally comprises more than 60% by weight, preferably more than 63% by weight, particularly preferably more than 65% by weight, of trioxane. For example, the stream III has the following composition: from 3 to 20% by weight of formaldehyde, from 10 to 30% by weight of water and from 60 to 75% by weight of trioxane. The stream X, which is obtained as side offtake stream from the first distillation column, comprises water, formaldehyde and trioxane, with water or formaldehyde generally being the main component. For example, the stream X has the following composition: from 10 to 50% by weight of formaldehyde, from 10 to 50% by weight of water and from 3 to 40% by weight of trioxane.

The stream II is preferably recirculated to the trioxane synthesis.

The streams I, III, V and VII can further comprise up to 15% by weight of low boilers. Typical low boilers which can be formed in the trioxane synthesis and the subsequent separation by distillation are methyl formate, methylal, bis(methoxymethyl)ether, methanol, formic acid and further hemiacetals and full acetals. To separate off these low boilers, a low boiler removal stage can optionally be carried out between the first and second distillation stages. Here, the low boilers are preferably separated off at the top of a low boiler removal column which is generally operated at a pressure of from 0.1 to 5 bar, preferably at a pressure of from 1.0 to 2.5 bar. In general, the low boiler removal column has at least 2 theoretical plates, preferably from 15 to 50 theoretical plates. In general, the stripping section of this column comprises from 25 to 90%, preferably from 50 to 75%, of the theoretical plates in this column. The content of the components having a boiling point lower than that of trioxane in the output from the bottom of the low boiler removal column is generally less than 5% by weight, preferably less than 2.5% by weight, particularly preferably less than 1.5% by weight.

In general, a low boiler removal is carried out.

The stream III is separated in a further distillation stage at a pressure of from 0.2 to 17.5 bar into a stream IV of essentially pure trioxane and a stream V comprising trioxane as main component together with water and formaldehyde. This second distillation stage is preferably carried out at from 2.5 to 10 bar. In general, this second distillation stage is carried out in a distillation column having at least 2 theoretical plates, preferably from 10 to 50 theoretical plates, with the stream IV being obtained as bottom offtake stream or as side offtake stream in the stripping section of the column and the stream V being obtained as overhead stream. In general, the stripping section of this distillation column has from 25 to 90%, preferably from 50 to 75%, of the theoretical plates of this column.

In general, the stream IV comprises from 95 to 100% by weight, preferably from 99 to 100% by weight, of trioxane and from 0 to 5% by weight, preferably from 0 to 1% by weight, of water and secondary components. Secondary components are, in particular, the abovementioned low boilers and also components having boiling points higher than that of trioxane. The content of water and secondary components in the trioxane stream IV is particularly preferably <0.1%. It can even be <0.01%. The stream V comprises, for example, from 5 to 20% by weight of formaldehyde, from 15 to 35% by weight of water and from 50 to 75% by weight of trioxane.

According to the invention, the stream IV is purified in at least one further trioxane distillation stage at a pressure at the top of from 0.5 to 2 bar, with purified trioxane being obtained as side offtake stream XII in the enrichment section of the column. This distillation column preferably has from 5 to 50, particularly preferably from 10 to 20, theoretical plates. The pressure at the top of the column is preferably from 1.0 to 1.5 bar. The side offtake stream obtained is preferably pure trioxane having a purity of >99.9% by weight, particularly preferably >99.99% by weight.

This stage c1) can be followed by a second trioxane distillation of the stream XII as stage c2). This stage is likewise carried out at a pressure at the top in the range from 0.5 to 2.0 bar, particularly preferably from 1.0 to 1.5 bar, with purified trioxane once again being obtained as side offtake stream in the enrichment section of the column. This further distillation column likewise preferably has from 5 to 50, particularly preferably from 10 to 20, theoretical plates. Polymerization-grade high-purity trioxane is obtained as side offtake stream.

The stream X and, if appropriate, a water-comprising stream IX are separated in a third distillation stage at a pressure of form 1 to 10 bar into a stream VI consisting essentially of water and a recycle stream VII comprising trioxane as main component together with water and formaldehyde. The water-comprising stream IX is, if appropriate, obtained as vapor offtake stream of a formaldehyde concentration unit configured as a vaporizer and comprises, for example, from 70 to 97% by weight of water and from 3 to 30% by weight of formaldehyde. The third distillation stage is preferably carried out at a pressure of from 2.5 to 6.5 bar. In general, the third distillation stage is carried out in a distillation column having at least two theoretical plates, preferably from 10 to 50 theoretical plates, with the water stream VI being obtained as bottom offtake stream or as side offtake stream from the column and the recycle stream VII being obtained as overhead stream. The stream X is preferably introduced in the upper region of the column, for example in the region of the uppermost third of the theoretical trays of the column, and the stream IX is introduced in the middle region of the column, for example in the region of the middle third of the theoretical trays of the column.

The water stream VI preferably comprises more than 95% by weight, particularly preferably more than 97% by weight, of water. For example, the stream VI comprises from 98 to 100% by weight of water, from 0 to 1% by weight of formaldehyde and from 0 to 1% by weight of secondary components.

The stream VII comprises, for example, from 10 to 55% by weight of formaldehyde, from 5 to 50% by weight of water and from 5 to 55% by weight of trioxane.

The stream VII can be recirculated partly or in its entirety to a point upstream of the first distillation stage; it is preferably recirculated essentially in its entirety to the first distillation stage. It can be introduced into the first distillation column either as a mixture with the recycle stream V or separately therefrom.

The present invention also provides a process for preparing trioxane from an aqueous formaldehyde solution, in which the feed stream I comprising formaldehyde, trioxane and water is prepared from an aqueous formaldehyde solution in an upstream trioxane synthesis stage and trioxane is subsequently separated from the stream I as described above.

The present invention also provides a process for preparing trioxane from an aqueous formaldehyde solution, in which the feed stream I comprising formaldehyde, trioxane and water is prepared from an aqueous formaldehyde solution in an upstream trioxane synthesis stage and trioxane is subsequently separated from the stream I as described above. As an alternative, the trioxane synthesis and the first distillation stage can be combined in a reactive distillation.

In an embodiment of the process of the invention, a stream XI comprising an aqueous formaldehyde solution is fed to an upstream trioxane synthesis stage and reacted at a temperature of generally from 70 to 130° C. in the presence of acidic homogeneous or heterogeneous catalysts such as ion exchange resins, zeolites, sulfuric acid and p-toluenesulfonic acid. This can be carried out in a distillation column or a vaporizer (reactive vaporizer). The product mixture of trioxane/formaldehyde and water is then obtained as a gaseous vapor offtake stream from the vaporizer or as overhead stream at the top of the column. The trioxane synthesis stage can also be carried out in a fixed-bed or fluidized-bed reactor over a heterogeneous catalyst, e.g. an ion exchange resin or zeolite.

In a further embodiment of the process of the invention, the trioxane synthesis stage and the first distillation stage are carried out as a reactive distillation in a reaction column. This can comprise a fixed catalyst bed comprising a heterogeneous acid catalyst in the stripping section. As an alternative, the reactive distillation can also be carried out in the presence of a homogeneous catalyst, in which case the acid catalyst is present together with the aqueous formaldehyde solution in the bottom of the column.

In general, the aqueous formaldehyde solution which is fed to the trioxane synthesis stage comprises from 30 to 85% by weight of formaldehyde and from 15 to 70% by weight of water. This solution can be obtained from an aqueous formaldehyde solution having a lower formaldehyde concentration in an upstream concentration step. The concentration step can, for example, be carried out in a vaporizer, preferably a falling film evaporator.

The upstream concentration step can be carried out, for example, as described in DE-A 199 25 870.

In an embodiment of the process of the invention, a stream VIII of an aqueous formaldehyde solution is concentrated in a vaporizer, preferably a falling film evaporator, to give the stream XI of aqueous formaldehyde solution having a higher formaldehyde concentration. The vapor offtake stream from the vaporizer, which is greatly depleted in formaldehyde, is fed as water-comprising stream IX into the third distillation stage. Stream VIII comprises, for example, from 40 to 60% by weight of formaldehyde and from 40 to 60% by weight of water. The concentrated stream XI comprises, for example, from 55 to 80% by weight of formaldehyde and from 20 to 45% by weight of water. The vapor offtake stream IX which has been depleted in formaldehyde comprises, for example, from 10 to 25% by weight of formaldehyde and from 75 to 90% by weight of water.

The resulting pure trioxane whose purity can be >99% by weight, >99.9% by weight or even >99.99% by weight, or the polymerization-grade high-purity trioxane is preferably used for preparing polyoxymethylene (POM), polyoxymethylene derivatives such as polyoxymethylene dimethyl ether (POM-DME) and diaminodiphenylmethane (MDA).

In addition, the invention relates to a method of separating formic acid from the mixture comprising formaldehyde, trioxane, water and formic acid by distillation. This makes an improvement in the crude yield of the trioxane process possible, and the trioxane can additionally be stabilized.

It is generally difficult to separate off formic acid which goes over together with trioxane on distillation. The formic acid is formed, for example, from formaldehyde by the Cannizzaro reaction, which also forms one equivalent of methanol. Since formic acid can catalyze the decomposition of trioxane, the effective removal of formic acid and, as a result, the suppression of trioxane decomposition are very important. As indicated above, a mixture having an approximately azeotropic composition of the main components trioxane, formaldehyde and water is separated in a distillation column operated under superatmospheric pressure at temperatures of up to >180° C. into pure trioxane in the output at the bottom and an azeotrope in the output at the top. Owing to the distillation conditions selected, the output from the bottom frequently comprises relatively large amounts of formic acid, for example 5000 ppm of formic acid. However, formic acid has a severely adverse effect on the polymerization of trioxane to polyoxymethylene (POM) and also leads to a deterioration in the POM quality, so that the maximum formic acid content should be greatly reduced.

According to the invention, this is preferably achieved by adding at least one tertiary amine and/or an imine or a mixture thereof which can deprotonate the formic acid and convert it into a salt in a catalytic amount or in an amount sufficient for salt formation with the entire amount of formic acid before or during the distillation and discharging the formic acid-amine salt formed in a liquid phase in the distillation bottoms.

It is possible to use individual amines or imines, mixtures of amines or imines or mixtures of amines and imines.

According to the invention, preference is given to using a tertiary amine or a mixture of tertiary amines which can deprotonate the formic acid and convert it into a salt.

The expression "tertiary amine" refers to a nitrogen-comprising compound in which all three hydrogen atoms of ammonia have been replaced by organic radicals. It can have an acyclic or cyclic structure, and a cyclic structure can be aliphatic or aromatic, e.g. as in the case of pyridine. The tertiary amine is preferably selected from among tri-$C_{1-3}$-alkylamines, cyclic or bicyclic aliphatic tertiary amines, imidazole and pyridine. The tertiary amine can be a trialkylamine if it has only one nitrogen atom. According to the invention, it is also possible for the tertiary amine to have a plurality of nitrogen atoms on each of which the hydrogen atoms have been replaced by organic radicals. It is also possible for the organic radicals, for example together with further heteroatoms such as nitrogen atoms, to form bicyclic structures. The tertiary amines used according to the invention preferably have two or three, in particular two, tertiary nitrogen atoms. Particular preference is given to a diazabicycloalkane compound or diazabicycloalkene compound. Particularly preferred examples are diazabicycloundecene (DBU) and triethylenediamine (TEDA, DABCO®).

The tertiary amine has a basicity which is sufficiently great for it to be able to deprotonate the formic acid and convert it into a salt. In addition, the tertiary amine is selected so that the formic acid-amine salt formed is present in a liquid phase (ionic liquid). To form such a salt, the molar ratio of tertiary nitrogen atoms to formic acid is preferably in the range from 1:1 to 3:1, particularly preferably in the range from 1:1 to 2:1, in particular about 1:1.

The basicity of the amine is important: a strong base is necessary to deprotonate the formic acid completely and form a low-melting, stable salt in the liquid phase. The removal of the formic acid from the product mixture greatly reduces the autocatalytic decomposition of trioxane. The presence of a low-melting salt (ionic liquid) enables solids handling to be avoided. Triethylenediamine is particularly advantageously used as base. The ammonium salt TEDA * HCOO can be separated off as high boiler and can be redissociated into TEDA and HCOOH or CO and $H_2O$ or $CO_2$ and $H_2$ at elevated temperatures in the gas phase. This makes catalytic use of the amine by recirculation in the process possible, i.e. the amine (or imine) is not consumed.

Since the tertiary amine has a stabilizing effect on trioxane, it is possible to make additional use of this stabilizing action. In this case, the amine is added in a molar excess over the formic acid, so that the trioxane is base-stabilized. The molar excess is preferably from 2-fold to 5-fold, i.e. from 2:1 to 5:1.

The formic acid-amine salt is preferably present as an ionic liquid at ambient temperature (25° C.).

In the distillation, the tertiary amine is preferably introduced into the feed, stripping section, enrichment section and/or bottom of at least one distillation column. Preference is given to adding it to the feed to at least one of the columns in the second and third distillation stages. Introduction into the second distillation stage is preferred.

The formic acid-amine salt is discharged with the distillation bottoms. It is then preferably subjected to a further distillation in which it is discharged from the bottom of the distillation column.

The formic acid-amine salt discharged can be decomposed by heating so as to recover the tertiary amine which can then be recirculated to the process. In this way, it is possible to circulate the tertiary amine without appreciable consumption occurring. This makes the process particularly economical. The decomposition of the formic acid-amine salt by heating is described, for example, in Angew. Chem. 82, 1970, No. 2, pages 73 to 77.

The invention is illustrated below with reference to the drawing.

Figure 1:
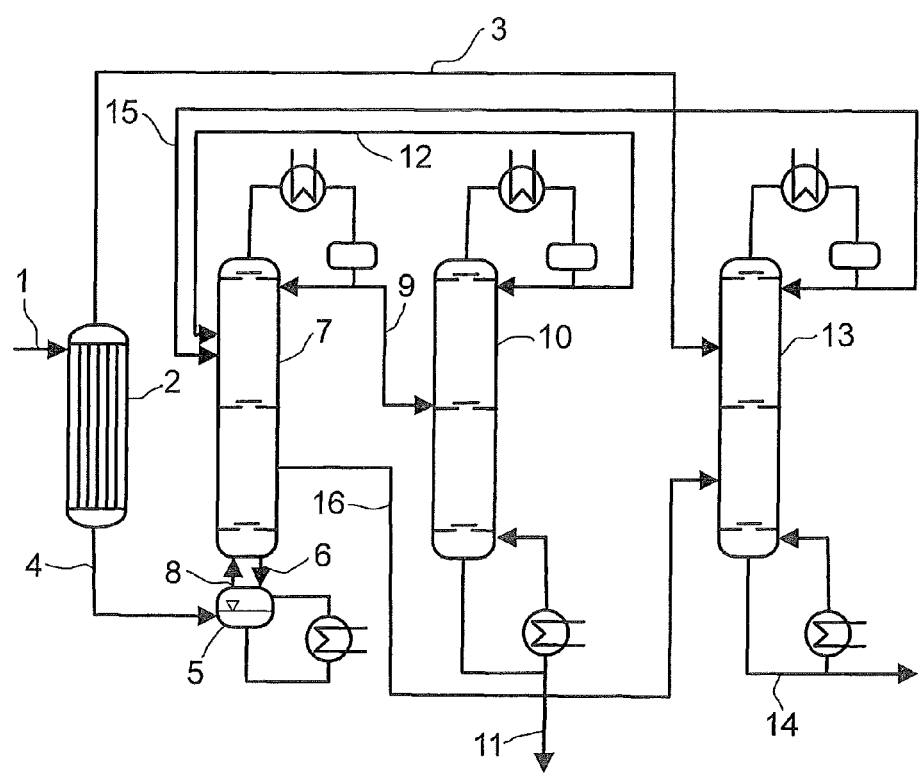
FIG. 1 shows, by way of example, an embodiment of the process of the invention.
Figure 2:
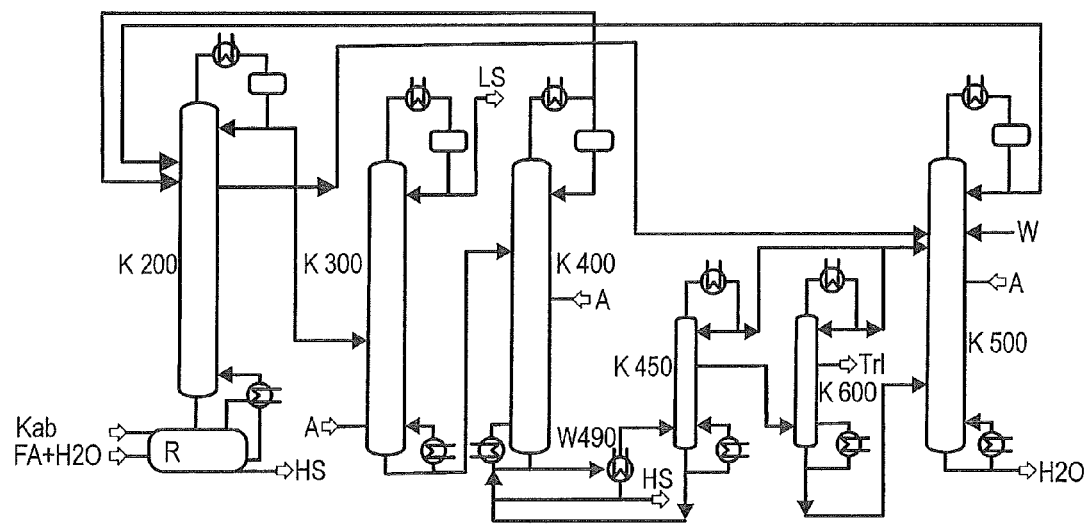
FIG. 2 shows an embodiment of the process of the invention in which the further distillation Stages K450 and K600 are shown.

An aqueous formaldehyde solution 1 (stream VIII) is fed to the vaporizer 2, for example a thin film evaporator, falling film evaporator or helical tube evaporator. An aqueous solution depleted in formaldehyde is obtained as vapor offtake stream 3 (stream IX) from the vaporizer, and a formaldehyde-rich aqueous solution is obtained as bottom offtake stream 4 (stream XI) from the vaporizer. This is fed together with the formaldehyde-rich bottom offtake stream 6 (stream II) from the first distillation column 7 to the trioxane synthesis reactor 5 which is configured as a vaporizer. The gaseous trioxane/formaldehyde/water mixture 8 (stream I) leaving the trioxane synthesis reactor is fed to the bottom of the first distillation column 7. The trioxane-rich overhead stream 15 (stream VII) from the third distillation column 13 is fed into the distillation column 7 in the vicinity of the top of the column. From the distillation column 7, a formaldehyde/water stream 6 (stream II) is taken off as bottom offtake stream, a formaldehyde/water/trioxane stream having a low water content 9 (stream III) is taken off as overhead stream and a water-rich formaldehyde/water/trioxane stream 16 is taken off as side offtake stream. Stream 6 is recirculated together with stream 4 to the reactor 5. The formaldehyde/water/trioxane stream having a low water content 9 is fed to the distillation column 10 and is there separated into a bottom offtake stream 11 (stream IV) consisting essentially of pure trioxane and an overhead stream 12 (stream V) comprising predominantly trioxane and also water and formaldehyde. The stream 12 is recirculated to the first distillation column. The water-rich formaldehyde/water/trioxane stream 16 and the aqueous vapor offtake stream having a low formaldehyde content 3 (stream IX) from the vaporizer 2 are fed to the third distillation column and separated there into a stream 14 (stream VI) which consists essentially of water and is discharged and the recycle stream 15 (stream VII) comprising predominantly formaldehyde and also water and trioxane. The stream IV is fed to one or two further distillation stages, as shown in FIG. 2.

EXAMPLE

In the computer simulation of the process shown in the figure, streams 4, 9, 11, 12, 3, 14, 15 and 16 having the compositions indicated in the tables were obtained. The following parameters were selected here: the first distillation stage is carried out at a pressure of from 0.7 bar in a column 7 having 10 theoretical plates. The reflux ratio is 0.8, the temperature at the top is 80° C. and the temperature at the bottom is 94° C. The second distillation stage is carried out at a pressure of 4.0 bar in a column 10 having 40 theoretical plates. The reflux ratio is 0.5, the temperature at the top is 146° C. and the temperature at the bottom is 181° C. The inlet 9 is located at the height of the 35th theoretical plate. The third distillation stage is carried out at a pressure of 6.0 bar in a column 13 having 10 theoretical plates. The reflux ratio is 1.5, the temperature at the top is 146° C. and the temperature at the bottom is 160° C. The inlet 3 is located at the height of the 8th theoretical plate.

|  | Stream | | | | | | | |
| --- | --- | --- | --- | --- | --- | --- | --- | --- |
|  | 4 (XI) | 9 (III) | 11 (IV) | 12 (V) | 3 (IX) | 14 (VI) | 15 (VII) | 16 (X) |
| Mass flow [kg/h] | 4.1 | 11.9 | 3 | 9.0 | 2.0 | 3.1 | 8.3 | 9.5 |
| Formaldehyde [% by weight] | 65.0 | 8.5 | <1 | 11.3 | 15.3 | <1 | 52.2 | 42.7 |
| Water [weight] | 35.0 | 21.5 | <1 | 28.7 | 84.7 | >99 | 22.6 | 35.2 |
| Trioxane [% by weight] | 0 | 70.0 | >99 | 60.0 | 0 | 0 | 25.2 | 22.1 |

FIG. 2 shows, by way of example, an embodiment of the process of the invention in which the further distillation stages K450 and K600 are shown. In the figure:

| Cat | Catalyst |
| --- | --- |
| FA | Formaldehyde |
| R | Reactor |
| HS | High boilers |
| A | Introduction of amine |
| Tri | Trioxane |
| LS | Low boilers |
| W | Water-comprising stream |

The concentration and reaction are carried out in the region of reactor R and column K200. The low boiler removal is carried out in the column K300. This is followed by the trioxane separation in the columns K400, K450 and K600. Water is separated off in the column K500.

In this embodiment, the reaction and concentration are carried out in separate apparatuses. As an alternative, reaction and concentration can be combined in the column K200, so that catalyst, formaldehyde and water are introduced at the bottom of the reactive distillation column while high boilers are discharged from the bottom of the columns.

The distillation columns can be connected so that the reactor output obtained in the trioxane synthesis is fed to the first distillation column K200 whose bottom offtake stream is, if trioxane synthesis and trioxane concentration are carried out in separate apparatuses, see FIG. 2, fed to the trioxane synthesis stage. Otherwise, if the trioxane synthesis takes place in the bottom region of the column, the bottom offtake stream is usually fed to the bottom vaporizer of the column. The trioxane-rich distillate from the first column is fed to a second distillation column K300 in which all components which interfere in the subsequent work-up steps and have boiling points lower than that of trioxane are separated off at the top, and the bottom output from the second column is fed to a third distillation column K400 in which crude trioxane is obtained via a side offtake in the stripping section or directly at the bottom offtake. The side offtake stream or the bottom output from K400 is fed into a fourth column K450 in the stripping section, preferably in the bottom region, and the pure trioxane obtained at the side offtake in the enrichment section of the column K450 is fed to the fifth column K600 in which polymerization-grade high-purity trioxane is obtained at a side offtake in the enrichment section. The overhead product from K400 is preferably fed to the sixth column K500 and particularly preferably to the first column K200 and also the side offtake of K200, possibly after mixing with a further water-comprising stream which results, for example, from concentration of a formaldehyde-comprising stream, subsequently to the sixth column K500 to give a water-comprising stream in which pure water is isolated via a side offtake stream in the stripping section or directly at the bottom offtake of the column. The overhead product is recirculated to the first column K200.

The bottom output from the fourth column K450 can be recirculated to the sixth column K500 or preferably to the second column K300 or particularly preferably to the third column K400.

The overhead stream from the fourth column K450 can be recirculated to the third column K400 or preferably to the second column K300 or particularly preferably to the sixth column K500.

The bottom output from the fifth column K600 can be recirculated to the third column K400 or preferably to the second column K300 or particularly preferably to the sixth column K500.

The overhead stream from the fourth column K450 can be recirculated to the third column K400 or preferably to the second column K300 or particularly preferably to the sixth column K500.

The crude trioxane taken off via the bottom or via a side offtake in the stripping section can be vaporized in one or more stages in the third column K400, see W490 in FIG. 2, so that the high boilers, e.g. formates, present in the crude trioxane as a result of the addition of the amine are separated off before the stream depleted in high-boiling components is fed, in gaseous or condensed form, into the stripping section, preferably directly into the bottom region, of the fourth column K450.

The output from the single-stage or multistage vaporization which has been enriched in high-boiling components can, except for a small purge stream which is fed to the sixth column K500 or discarded, be recirculated to the third column K400 and fed into the stripping section, preferably into the bottom of the column.

The enrichment section of the distillation column K200 can, in order to concentrate the trioxane formed in the synthesis, have from 10 to 100%, preferably from 50 to 100%, of the theoretical plates of the column.

The enrichment section of the distillation column K300 can, in order to separate off the components in the reactor output which have boiling points lower than that of trioxane, have from 25 to 95%, preferably from 50 to 75%, of the theoretical plates of the column.

The stripping section of the distillation column K400 can, in order to obtain crude trioxane, have from 25 to 100%, preferably from 75 to 100% and particularly preferably from 90 to 100%, of the theoretical plates of the column.

The enrichment section of the distillation column K450 can, in order to obtain pure trioxane, have from 25 to 100%, preferably from 75 to 100% and particularly preferably from 90 to 100%, of the theoretical plates of the column.

The enrichment section of the distillation column K600 can, in order to obtain polymerization-grade high-purity trioxane, have from 25 to 100%, preferably from 75 to 100% and particularly preferably from 90 to 100%, of the theoretical plates of the column.

The stripping section of the distillation column K500 can, in order to obtain a water-comprising stream, have from 25 to 100%, preferably from 75 to 100% and particularly preferably from 90 to 100%, of the theoretical plates of the column.

The distillation columns can be provided with ordered packings, random packing elements or trays and be thermally coupled.

The thermally coupled distillation columns can each be equipped with a dedicated vaporizer and condenser.

The two thermally coupled columns can be operated at different pressures, and only liquid can be conveyed in the connecting streams between the two columns.

The reactor output fed to the first column (K200) can be introduced in liquid or vapor form, preferably in vapor form, into the stripping section or the bottom region, preferably directly into the bottom region.

The basic amine/imine can be introduced into the second column K300, preferably into the third column K400, but also additionally into the sixth column K500.

The invention is illustrated further by the following examples of amine addition.

Comparative Example 1.0 g/h of a composition comprising 69.8% by weight of trioxane, 292 ppm by weight of formic acid and formaldehyde and water as balance was fed to a distillation column operated at a temperature of about 182° C. and a pressure at the top of 5.5 bar, 0.91 g/h of a composition comprising 59.7% by weight of trioxane, 501 ppm by weight of formic acid together with formaldehyde and water as balance was obtained at the top, while 0.09 kg/h of a composition comprising 99.58% by weight of trioxane and 4200 ppm by weight of formic acid was obtained at the bottom. The trioxane decomposition was 9.3%.

Example 1

1.0 kg/h of a composition comprising 65.8% by weight of trioxane, 350 ppm by weight of formic acid and formaldehyde and water as balance was fed to a distillation column operated at a pressure at the top of 5.5 bar and a temperature of about 182° C. In addition, 0.3 ml/h of diazabicycloundecene were mixed into the feed. 0.84 kg/h of a composition comprising 58.1% by weight of trioxane, 603 ppm by weight of formic acid and formaldehyde and water as balance was taken off at the top, while 0.16 kg/h of a composition comprising 99.99% by weight of trioxane and 100 ppm by weight of formic acid was obtained at the bottom. The trioxane decomposition was 1.5%. The bottom output could be separated in a further vaporizer into trioxane at the top and formic acid-amine salt at the bottom, with the salt being able, after decomposition of the formate, to be recirculated as amine.

The examples show that the decomposition of trioxane could be prevented effectively and the yield and purity of the trioxane were significantly improved.

The addition of amine is particularly advantageous in the three-stage distillation sequence according to the invention.

The invention claimed is:

1. A process for separating trioxane from a feed stream I comprising formaldehyde, trioxane and water, wherein
   a) a feed stream I comprising formaldehyde as main component and trioxane and water as secondary components is provided,
   b) the feed stream I, a recycle stream V and a recycle stream VII comprising formaldehyde as main component and water and trioxane as secondary components are fed into a first distillation stage and distilled at a pressure of from 0.1 to 2.5 bar to give a stream II comprising formaldehyde as main component and water as secondary component and a stream III comprising trioxane as main component and water and formaldehyde as secondary components and a stream X comprising water, trioxane and formaldehyde,
   c) the stream III is, if appropriate after removal of low boilers from the stream III in a low boiler removal stage, distilled in a second distillation stage at a pressure of from 0.2 to 17.5 bar, with the pressure in the second distillation stage being from 0.1 to 15 bar higher than the pressure in the first distillation stage, to give a stream IV consisting essentially of trioxane and the recycle stream V comprising trioxane as main component and water and formaldehyde as secondary components,
   c1) the stream IV is purified in at least one further trioxane distillation stage at a pressure at the top of from 0.5 to 2 bar to give purified trioxane as side offtake stream XII in the enrichment section of the column,
   d) the stream X and, if appropriate, a stream IX comprising water as main component obtained in the concentration of aqueous formaldehyde solution are fed into a third distillation stage and distilled at a pressure of from 1 to 10 bar to give a stream VI consisting essentially of water and a recycle stream VII comprising formaldehyde as main component and water and trioxane as secondary components.

2. The process according to claim 1, wherein stage c1) is followed by a second trioxane distillation of the stream XII as stage c2) at a pressure at the top in the range from 0.5 to 2.0 bar to give further purified trioxane as side offtake stream in the enrichment section of the column.

3. The process according to claim 1, wherein, in the distillation stages c1) and c2), the stream IV and the stream XII, respectively, are fed into the bottom region of the distillation stages.

4. The process according to claim 1, wherein at least one tertiary amine and/or an imine or a mixture thereof which can deprotonate formic acid and convert it into a salt is added to the mixture comprising formaldehyde, trioxane, water and formic acid which is fed to the second and/or third distillation stage in a catalytic amount or in an amount sufficient to form a salt with the entire amount of formic acid before or during the distillation and the formic acid-amine salt formed is discharged in a liquid phase in the distillation bottoms.

5. The process according to claim 4, wherein the amine is added in a molar excess over the formic acid so that the trioxane is base-stabilized.

6. The process according to claim 4, wherein the tertiary amine is selected from among tri-$C_{1-3}$-alkylamines, cyclic or bicyclic aliphatic tertiary amines, imidazole and pyridine, preferably from among diazabicycloundecene (DBU) and triethylenediamine (TEDA, DABCO).

7. The process according to claim 4, wherein the formic acid-amine salt discharged with the distillation bottoms is subjected to a further distillation in which it is discharged from the distillation bottoms and/or the formic acid-amine salt discharged is subjected to heating so that the tertiary amine is recovered and can be recirculated to the process.

8. The process according to claim 1, wherein a low boiler removal stage in which low boilers selected from the group consisting of methyl formate, methylal, bis(methoxymethyl) ether and methanol are separated off from the stream III is carried out between the first distillation stage and the second distillation stage.

9. The process according to claim 1, wherein the streams I-VII and X have the following compositions:
Stream I: from 40 to 80% by weight of formaldehyde, from 20 to 59% by weight of water, from 1 to 30% by weight of trioxane;
Stream II: from 55 to 85% by weight of formaldehyde, from 15 to 45% by weight of water, from 0 to 5% by weight of trioxane;
Stream III: from 3 to 20% by weight of formaldehyde, from 10 to 30% by weight of water, from 60 to 75% by weight of trioxane;
Stream IV: from 95 to 100% by weight of trioxane, from 0 to 5% by weight of water and secondary components;
Stream V: from 5 to 20% by weight of formaldehyde, from 15 to 35% by weight of water, from 50 to 75% by weight of trioxane;
Stream VI: from 0 to 1% by weight of formaldehyde, from 99 to 100% by weight of water;
Stream VII: from 10 to 55% by weight of formaldehyde, from 5 to 50% by weight of water, from 5 to 55% by weight of trioxane;
Stream X: from 10 to 50% by weight of formaldehyde, from 10 to 50% by weight of water, from 3 to 40% by weight of trioxane;
with the streams I, III, V and VII being able to further comprise up to 15% by weight of low boilers selected from the group consisting of methyl formate, methylal, bis(methoxymethyl) ether and methanol.

10. A process for preparing trioxane from an aqueous formaldehyde solution, wherein a stream XI of an aqueous formaldehyde solution from a trioxane synthesis stage is fed in and reacted under acid conditions to give the stream I and trioxane is separated from the stream I by the process according to claim 1, where the stream XI can be obtained from a stream VIII of an aqueous formaldehyde solution having a lower formaldehyde concentration by concentration in a vaporizer.

\* \* \* \* \*